United States Patent
Ruizendaal

(10) Patent No.: US 6,296,410 B1
(45) Date of Patent: Oct. 2, 2001

(54) APPARATUS FOR DISPENSING AN AMOUNT OF FLUID COOLANT AND A DISPENSING UNIT

(75) Inventor: Johanna C. Ruizendaal, Dongen (NL)

(73) Assignee: Wartner B.V., Oosterhout (NL)

( * ) Notice: Subject to any disclaimer, the term of this patent is extended or adjusted under 35 U.S.C. 154(b) by 0 days.

(21) Appl. No.: 09/647,216
(22) PCT Filed: Mar. 30, 1999
(86) PCT No.: PCT/NL99/00187
    § 371 Date: Sep. 28, 2000
    § 102(e) Date: Sep. 28, 2000
(87) PCT Pub. No.: WO99/49797
    PCT Pub. Date: Oct. 7, 1999

(30) Foreign Application Priority Data

| Mar. 30, 1998 | (NL) | 1008753 |
| Apr. 16, 1998 | (NL) | 1008902 |
| Dec. 9, 1998 | (NL) | 1010774 |

(51) Int. Cl.[7] .................................... B05C 17/005
(52) U.S. Cl. ............... 401/119; 222/402.13; 401/130; 401/190; 401/191; 401/204; 401/207
(58) Field of Search .................... 401/119, 118, 401/130, 127, 190, 191, 200, 204, 207; 222/402.13

(56) References Cited

U.S. PATENT DOCUMENTS

| 3,818,911 | * | 6/1974 | Fournier | 401/130 X |
| 4,969,854 | * | 11/1990 | Katsuda et al. | 401/190 |
| 5,340,031 | * | 8/1994 | Neuhaus et al. | 401/190 X |
| 5,516,505 | | 5/1996 | McDow | |
| 5,567,073 | * | 10/1996 | De Laforcade et al. | 401/190 |
| 5,573,340 | * | 11/1996 | Gueret | 401/119 X |
| 5,597,255 | | 1/1997 | Yager et al. | |
| 5,899,623 | * | 5/1999 | De Laforcade | 401/190 |

FOREIGN PATENT DOCUMENTS

| 0608954 | 8/1994 | (EP) . |
| 2422564 | 11/1979 | (FR) . |
| 1008391 | 3/1998 | (NL) . |

OTHER PUBLICATIONS

Information Leaflet Wartner "Wrattenverwijderaar" (XP–002107834) (undated).

* cited by examiner

Primary Examiner—David J. Walczak
Assistant Examiner—Kathleen J. Prunner
(74) Attorney, Agent, or Firm—Banner & Witcoff, Ltd.

(57) ABSTRACT

A device for administering a quantity of liquid cooling agent, contained in an aerosol container provided with a normally closed valve has an operating device for temporarily opening the valve. The positioning device positions at least a part of an administering element so that the cooling agent leaving the valve can reach the administering element. The cooling agent leaving the valve reaches that part of the administering element which comes into contact with a wart to be frozen, so that it is used effectively. According to a first preferred embodiment the positioning device has a chamber which is connects to the valve and into which the cooling agent is carried when the valve is operated. The chamber is adapted to receive of at least a part of the administering element.

29 Claims, 3 Drawing Sheets

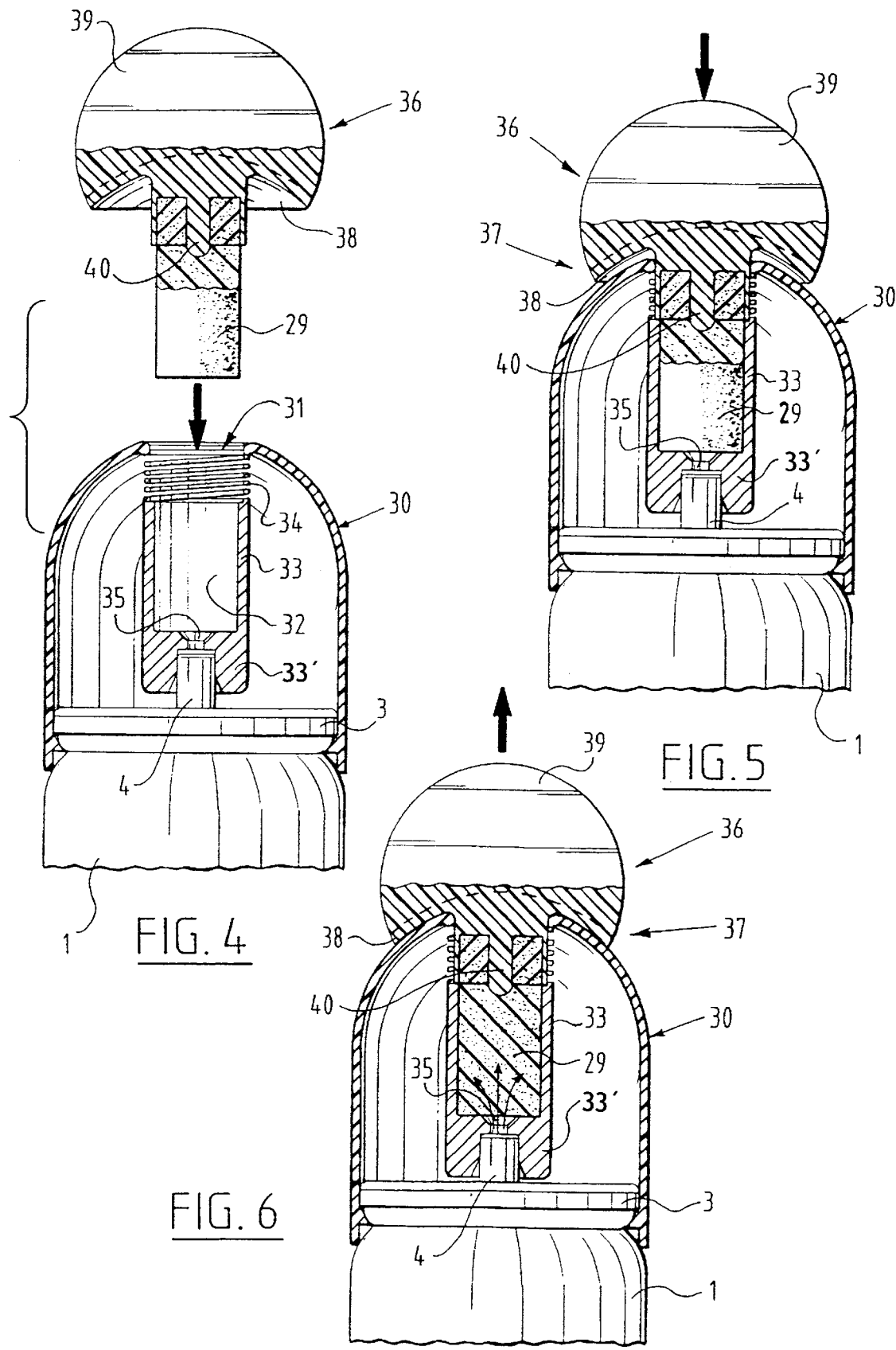

APPARATUS FOR DISPENSING AN AMOUNT OF FLUID COOLANT AND A DISPENSING UNIT

The present invention relates to a device for administering a quantity of liquid cooling agent, comprising:
a container for holding the fluid coolant;
a normally closed valve connected to the container; and
operating means for temporarily opening the valve.

Such a device is known from the patent publication EP-B-0 608 954.

In this known device use is made of a thin pipe which is connected to the valve and which is provided on its free end with a foamed porous body. The pipe debouches into the interior of the foamed body.

Such a device is applied for instance in the removal of warts. A quantity of cooling agent applied to the administering element is herein pressed onto the wart, whereafter this latter freezes and disappears. This method is generally known per se; it is performed by general practitioners using liquid nitrogen.

During use of this known device the valve is depressed and cooling agent enters the interior of the foamed body via the valve and the pipe. Inside the foamed body the cooling agent must then move toward the outside in liquid or gaseous form. This results in a reduced effectiveness; the cooling agent must after all spread inside the foamed body, so that only a part of the cooling agent reaches the location where the foamed body comes into contact with the wart.

The object of the present invention is to provide such a device wherein the above stated drawbacks are obviated.

This object is achieved by positioning means for positioning at least a part of the administering element so that cooling agent leaving the valve can reach the administering element.

By means of this measure the greater part of the cooling agent leaving the valve reaches that part of the administering element which comes into contact with the wart, so that it is used effectively.

According to a first preferred embodiment the positioning means comprise a chamber which is connected to the valve and into which the cooling agent is carried when the valve is operated, which chamber is adapted for placing of at least a part of the administering element.

It will be apparent that this embodiment results in a particularly effective administration; the cooling agent is able to spread inside the chamber and can exit to the outside only with difficulty.

An even more attractive embodiment is obtained when the operating means are only coupled to the valve when the administering element is placed in the cavity. This measure results in the operating means only being effective when an administering element is placed in the cavity. This means that the valve cannot be operated without administering element, thus preventing for instance children spraying the cooling agent, with the dangers this involves.

Another advantage is that only when an administering element is placed in the correct manner can this administering element be wetted with the cooling agent. This also improves the effectiveness.

According to yet another embodiment the operating means are integrated into the chamber and the operating means are activated when an administering element is placed in the chamber.

According to a specific embodiment hereof the chamber is placed with its shaft directly onto the valve and the direction of movement of the administering element to be moved into the chamber corresponds with the operating direction of the valve.

The present invention will be elucidated hereinbelow with reference to the annexed drawings, in which:

FIG. 4 is a cross-sectional view of a second embodiment prior to insertion of an administering element;

FIG. 5 is a view corresponding with FIG. 4, wherein the administering element has been placed into the chamber;

FIG. 6 shows a view corresponding with FIGS. 4 and 5 wherein the valve is operated by means of the administering element;

Figure 1:
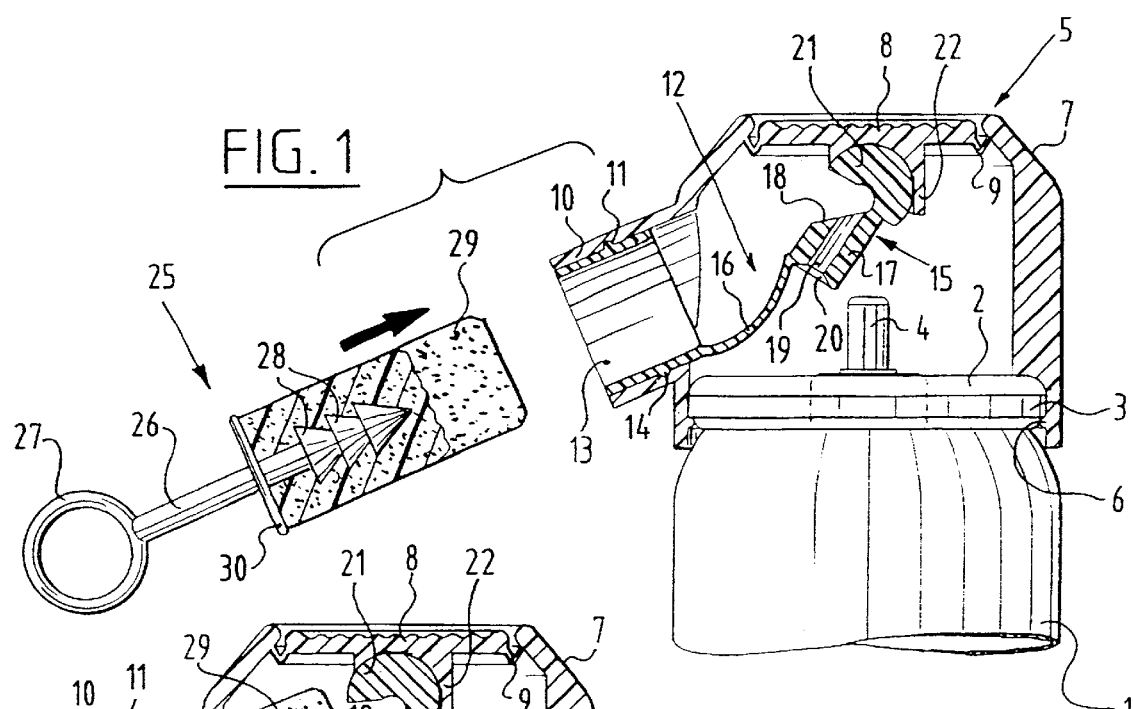
FIG. 1 shows a side view of a device according to the present invention wherein a part of the device is shown in cross-section, this in the situation where the administering element is inserted.

FIG. 1 shows an aerosol container 1 which is closed in the usual manner at its top with a cover 2 seam-folded in the form of a beaded edge 3 round the upper edge of aerosol container 1. Arranged in the cover is a valve 4 which, when pressed at the top, connects the interior of the aerosol container to the outside environment with a small opening in its top side.

Such an aerosol container is generally known. On the top of aerosol container 1 is placed a cap which is designated as a whole with 5. This cap engages under beaded edge 3 by means of an internal ring 6 arranged for this purpose. The cap is substantially cylindrical and is provided on one side with a spout 10. The upper part of cap 5 is provided with a conical rounding 7 and a pressing surface 8 is arranged in the centre of the upper side of cap 5. Pressing surface 8 is connected to the rest of cap 5 by means of an annular, attenuated part 9 of V-shaped cross-section. As a result of the thin part 9 it is possible to press cap 5 downward. Thin part 9 herein acts as a kind of hinge.

Spout 10 is annular and provided on its inside with a groove 11. The part of the cap described up to this point is manufactured integrally from a suitable plastic by means of for instance injection moulding or other design technique.

An accessory designated in its entirety by 12 is placed in the interior of spout 10. Accessory 12 is formed in the first instance by a cylindrical part 13 which fits clampingly inside spout 10 and is provided with an edge 14 which fits into groove 11. Fixation of cylinder 13, and therewith of the whole accessory 12, is hereby obtained.

It is also possible however for the accessory to be manufactured with the cap as a single injection moulded part.

Accessory 12 further comprises a coupling piece 15 connected to cylinder 13 by means of,an elastic strip 16. Coupling piece 15 is formed by a cylindrical part 17 which is provided with a chamfer surface 18 on its top side and in which a channel 19 is arranged. A conical outlet 20 is further arranged on the underside. On its top side the coupling piece 15 comprises a hemispherical part 21 which fits into a correspondingly formed engaging part 22 formed on the underside of pressing surface 8.

Figure 2:
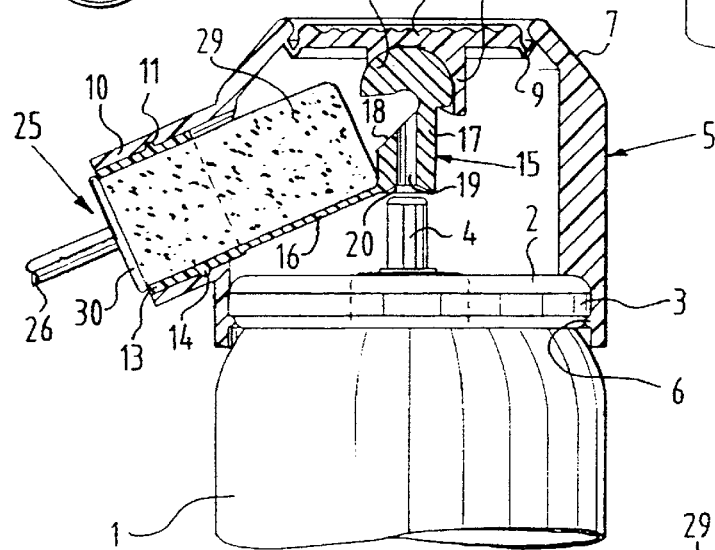
FIG. 2 is a view corresponding with FIG. 1, wherein the administering element is placed in the chamber.

The length and thickness of connecting strip 16 are such that in the normal situation coupling piece 15 occupies the position shown in FIG. 1. However, when an administering element is pushed into cylinder 13, strip 16 is straightened by the administering element being pressed against the underside of cylindrical part 17. The situation is then obtained as shown in FIG. 2.

The administering element, designated in its entirety 25, essentially comprises a rod-like carrier 26 manufactured from plastic on which is mounted a handle 27. On the free end of rod-like carrier 26 are arranged hooks 28 onto which an absorption element 29 made of foam plastic is pushed to a position against a wall 30.

Although the present invention is particularly dimensioned for the use of a foam plastic, it is of course possible to use other materials such as rolled-up wadding, paper other cellulose products, spongy structures and so on.

Instead of a plastic carrier 26 provided with a handle it is of course also possible to make use of other carriers such as wooden sticks and so on.

The operation of the present invention will now be elucidated. In the situation shown in FIG. 1 the administering element 25 has not yet been placed in the space formed for this purpose. Coupling piece element 15 is therefore located in the situation shown in FIG. 1, so that no coupling can be made between pressing surface 8 and valve 4. When in the drawn situation the pressing surface 8 is pressed in, valve 4 is not therefore operated, which prevents the cooling agent being wasted or hazardous situations arising.

When administering element 25 is then pushed into cylinder 13 and pushed further in until the absorption element 29 presses on cylinder 17 and pushes it so far that cylinder 17 extends in the line of valve 4, the situation is obtained as shown in FIG. 2.

It is otherwise possible to fix the administering element temporarily in the cylinder by means of a snap connection.

Figure 3:
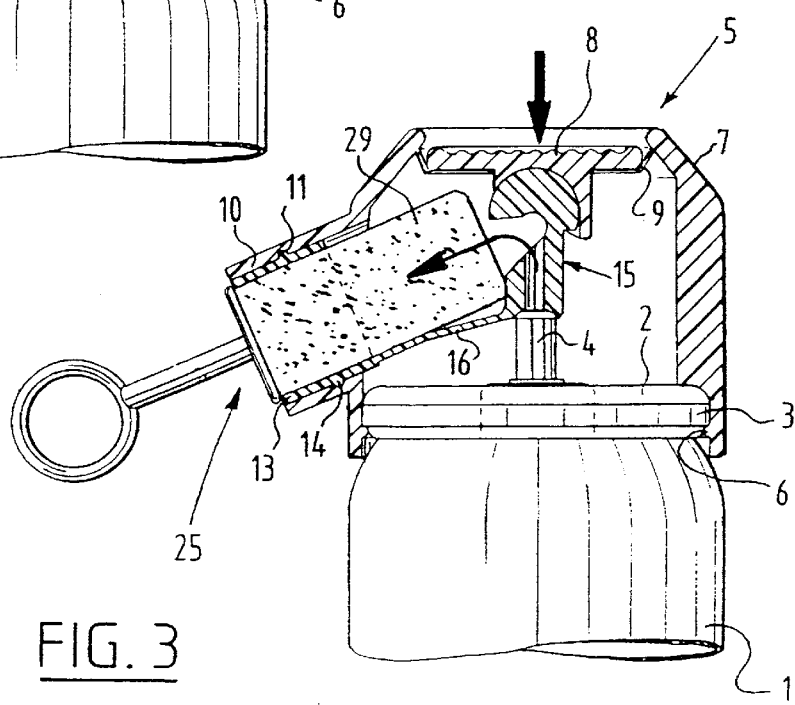
FIG. 3 shows a view corresponding with FIGS. 1 and 2 during operation of the valve.

Absorption element 29 is then situated in the positioning chamber formed by cylinder 13. When in the shown situation the pressing surface 8 is depressed a coupling is created between pressing surface 8 and valve 4, so that the cooling liquid can flow out of valve 4 and the situation is obtained as shown in FIG. 3.

The cooling agent then flows through channel 19 and arrives in the administering space where it will enter absorption element 29 and spread through the foam. An almost complete absorption of the cooling agent into absorption element 29 herein takes place so that absorption element 29 is as it were saturated with cooling agent.

When the administering element is subsequently moved out of chamber 13 and absorption element 29 enters open space, the cooling agent will begin to evaporate, whereby cooling occurs and, when the foam is then placed on a wart, it will be frozen, whereafter it will disappear after a period of time.

It would be possible to depress the operating element for a long time, whereby the administering element would become supersaturated with cooling agent and could begin to drip when removed.

This is prevented in that if the operating element is depressed for too long the cap construction also freezes and the coupling between operating element and valve is broken.

In the embodiment shown in FIGS. 4–6 a cap designated as a whole with 30 is fixed clampingly on the beaded edge 3 of aerosol container 1. Cap 30 takes a hemispherical form on its top side and provided in the centre with an opening 31. This opening 31 connects onto a chamber 32 which is enclosed by a cylinder 33 which is connected to the cap by means of a yielding element in the form of a spring 34. There therefore exists the option of integral moulding of cap together with cylinder 33 and spring 34. Chamber 32 is closed on its underside by a cylindrical body 33' which fits over valve 4. The design is herein such that the valve is activated when body 33' moves downward together with cylinder 33. An opening 35 is therefore arranged in the body 33' such that the bottom defines a shoulder surrounding opening 35. Use is further made in this embodiment of a different form of the administering element. Administering element 36 is formed by a carrier 37 and a piece of absorption element 29.

Carrier 37 is formed by a plate 38 with the shape of a part of a surface of a sphere on which is fixed a holding plate 39. It will be apparent that holding plate 39 can take other forms. On its underside plate 38 is provided with fingers 40 with which a piece of absorption element 29 is held. It is also possible here to make use of a mandrel (not shown) corresponding to the mandrel of the embodiment of FIG. 1.

It is also possible in this embodiment to make use of absorption element 29 having two parts of differing density or having a semi-open structure.

The above shown embodiment has the advantage that absorption element 29 can here also be removed easily after use and can be relaced by another piece.

When administering element 36 is pushed into the opening 31, wherein chamber 32 is filled for a large part but not completely by absorption element 29, fingers 40 have the function of pressing against an upper edge of cylinder 33. As shown in FIG. 6, the valve is hereby operated so that liquid pushes out of the aerosol into the foam.

Plate 38 has the further function here that it provides a good closure, so that the liquid leaving the aerosol cannot reach the fingers. For discharge of the gases created during evaporation of the aerosol and the thereby resulting overpressure, arrangement of apertures in the actual cap 30 can also be considered. This is not hazardous since the hands are not in contact with the cap during use of the device.

For a further increase in safety the use of a childproof operation can be considered. According to an embodiment not shown in the drawings this is possible by using an additional cap which is arranged round cap 30. This can be provided in per se known manner with a childproof closure, so that it has to be pressed in for instance before it can be screwed off.

Figure 7:
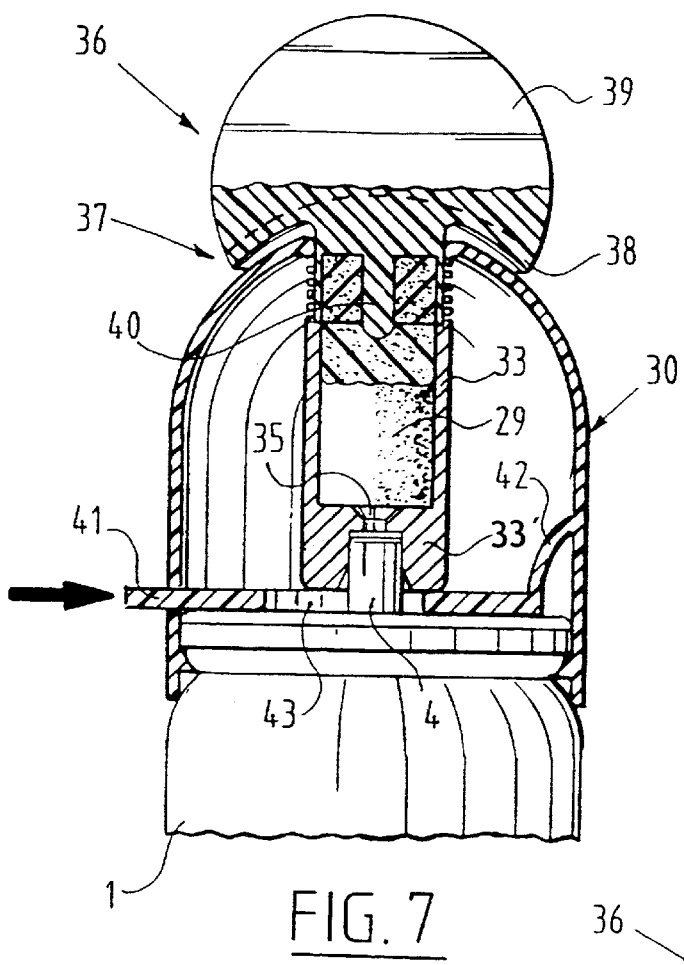
FIG. 7 is a view corresponding with FIG. 5 of a variant of the embodiment shown in FIGS. 4, 5 and 6.
Figure 8:
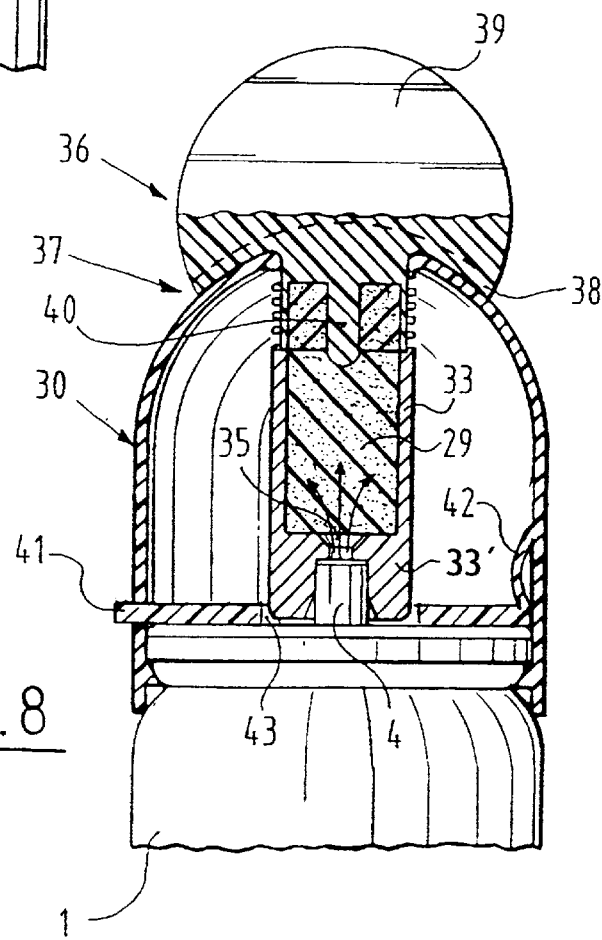
FIG. 8 is a view corresponding with FIG. 6 of the embodiment shown in FIG. 7.

It is also possible however, as shown in FIGS. 7 and 8, to apply another form of childproof safety device. Use is made herein of a slide element 41 connected to cap 30 by means of a resilient connection 42, wherein the slide element protrudes through an opening arranged in the other side of cap 30. An opening 43 is further arranged in the slide element. In the normal rest situation shown in FIG. 7 the valve cannot be operated because the combination of cylinder 33 and body 33' cannot be moved downward. This is prevented by a part of slide element 41. However, when slide element 41 is pressed inward, wherein the situation is obtained as shown in FIG. 8, it is then possible to operate the valve. This provides a simple and adequate measure against undesired operation by children.

It will be apparent that it is possible to vary in diverse ways from the present preferred embodiment without departing from the invention.

What is claimed is:

1. A device for administering a quantity of liquid cooling agent, comprising:

an aerosol container for holding the liquid cooling agent;

a normally closed Valve connected to the container;

operating means for temporarily opening the valve; and an administering element, comprising an absorption element and a carrier, the administering element being separable from the rest of the device, characterized in that
the device comprises positioning means for positioning at least a part of the absorption element in a position wherein cooling age,it leaving the valve can directly reach the absorption element.

2. A device as claimed in claim 1, characterized in that the positioning means comprise a chamber which is connected to the valve and into which the cooling agent is carried when the valve is operated, which chamber is adapted for placing of at least a part of the absorption element.

3. A device as claimed in claim 2, characterized in that the operating means are adapted to be coupled to the valve only when the absorption element is placed in the chamber.

4. A device as claimed in claim 3, characterized in that
the operating means comprise a movable element,
a displaceable coupling piece is movable between a first position, in which the coupling piece couples the operating means to the valve, and a second position in which this is not the case,
that the coupling piece is normally situated in the second position and the coupling piece is only caused to move to the first position by placing the absorption element in the positioning means.

5. A device as claimed in claim 4, characterized in that the coupling piece is connected by a resilient element to the container and that the resilient element is adapted to urge the coupling piece to the second position.

6. A device as claimed in claim 5, characterized in that the resilient element, the coupling piece and the positioning means are formed integrally.

7. A device as claimed in claim 6, characterized in that the resilient element, the coupling piece and the positioning means are placed clampingly in an otherwise integrally manufactured cap unit with the operating means integrated therein which is fixable on the container by means of a snap connection.

8. A device as claimed in claim 5, characterized in that the resilient element is adapted to at least partially transfer the force of the absorption element to the coupling piece.

9. A device as claimed in claim 4, characterized in that the coupling piece is always coupled to the operating means.

10. A device as claimed in claim 9, characterized in that the coupling piece is provided on its side directed toward the operating means with a hemispherical part.

11. A device as claimed in claim 4, characterized in that the coupling piece is provided with a channel for guiding the liquid cooling agent from the valve to the absorption element positioned by the positioning means.

12. A device as claimed in claim 11, characterized in that the channel is connected to the outlet opening of the valve only in the first position of the coupling piece.

13. A device as claimed in claim 3, characterized in that the coupling between the operating means and the valve is broken when the absorption element arranged in the container is frozen.

14. A device as claimed in claim 2, characterized in that the operating means are integrated into the chamber and that the operating means are activated when the absorption element is placed in the chamber.

15. A device as claimed in claim 14, characterized in that the chamber is placed with its axis directly inline with the valve and the direction of movement of the absorption element to be moved into the chamber corresponds with the operating direction of the valve.

16. A device as claimed in claim 15, characterized in that the charter is cylindrical and is provided on its inside with a shoulder.

17. A device as claimed in claim 16, characterized in that the chaser is connected by a yielding element to a cap placed on the container.

18. A device as claimed claim 14, characterized in that the device is provided with a childproof safety device.

19. A device as claimed in claim 18, characterized in that the childproof safety device comprises a cover fixable onto the cap by means of a childproof lock.

20. A device as claimed in claim 18, characterized in that the childproof safety device comprises an element normally preventing depressing of the valve and enabling depressing of the valve from outside counter to spring pressure.

21. A device as claimed in claim 14, characterized in that at least a part of the absorption element fits into the chamber.

22. A device as claimed in claim 21, characterized in that the absorption element is fixable in the chamber by means of a snap connection.

23. A device as claimed in claim 1 wherein at least a part of the administering element can be positioned by the positioning means.

24. A device as claimed in claim 1 wherein the administering element is adapted for at least partial positioning by tile positioning means and comprises:
a carrier;
a handle connected to the carrier;
the absorption element being connected to the carrier, wherein at least a part of the absorption element is adapted to be positioned by the positioning means, characterized in that the absorption element is releasably connected to the carrier.

25. A device element as claimed in claim 24, characterized in that the carrier comprises a mandrel which is adapted to be pressed into the absorption element.

26. A device as claimed in claim 24, characterized in that the carrier comprises a plate which is adapted to close a gap between the carrier and the absorption element.

27. A device as claimed in claim 24, characterized in that the absorption element is manufactured from foam plastic with a semi-open structure.

28. A device as claimed in claim 27, characterized in that the absorption element comprises two parts of mutually differing density.

29. A device as claimed in claim 24, characterized in that the absorption element is manufactured from paper.

* * * * *